US006328929B1

(12) United States Patent
Code

(10) Patent No.: US 6,328,929 B1
(45) Date of Patent: Dec. 11, 2001

(54) METHOD OF DELIVERING DISINFECTANT IN AN ABSORBENT SUBSTRATE

(76) Inventor: Kenneth Reay Code, 6309-187 Street, Edmonton, Alberta (CA), T5T 2R7

( * ) Notice: Subject to any disclaimer, the term of this patent is extended or adjusted under 35 U.S.C. 154(b) by 0 days.

(21) Appl. No.: 09/375,198

(22) Filed: Aug. 16, 1999

(51) Int. Cl.$^7$ ........................................................ A61L 1/00
(52) U.S. Cl. ................... 422/29; 422/29; 422/37; 423/303; 503/200; 503/201; 503/202
(58) Field of Search ................. 422/29, 37; 423/303; 503/200, 201, 202

(56) References Cited

U.S. PATENT DOCUMENTS

| 4,006,251 | * | 2/1977 | Taylor | 424/328 |
|---|---|---|---|---|
| 4,355,021 | | 10/1982 | Mahl et al. | 424/28 |
| 4,363,322 | | 12/1982 | Andersson | 128/155 |
| 4,756,937 | | 7/1988 | Mentzer | 428/35 |
| 4,822,595 | * | 4/1989 | Corliss et la. | 424/61 |
| 5,037,485 | * | 8/1991 | Chromecek et al. | 134/7 |
| 5,084,434 | * | 1/1992 | Kulisz | 503/201 |
| 5,104,660 | | 4/1992 | Chvapil et al. | 424/445 |
| 5,104,782 | * | 4/1992 | Seto et al. | 430/551 |
| 5,372,766 | | 12/1994 | Roe | 264/126 |

FOREIGN PATENT DOCUMENTS

| 2191928 | 12/1996 | (CA) . |
| 2201825 | 4/1997 | (CA) . |
| 0 651 983 A1 | 5/1995 | (EP) . |

* cited by examiner

Primary Examiner—Robert J. Warden, Sr.
Assistant Examiner—Imad Soubra
(74) Attorney, Agent, or Firm—Davis & Bujold, P.L.L.C.

(57) ABSTRACT

A method of delivering disinfectant in an absorbent substrate. A first step involves intermixing a first reactant chemical with a first ink. A second step involves intermixing a second reactant chemical with a second ink. A third step involves printing a first pattern on an absorbent substrate with the first ink. A fourth step involves printing a second pattern on the absorbent substrate with the second ink. The second pattern is positioned in close proximity to the first pattern, such that when the first pattern and second pattern are exposed to water an intermixing of the first reactant chemical and the second reactant chemical occurs to produce an aerosol disinfectant.

2 Claims, 2 Drawing Sheets

METHOD OF DELIVERING DISINFECTANT IN AN ABSORBENT SUBSTRATE

FIELD OF THE INVENTION

Figure 1:
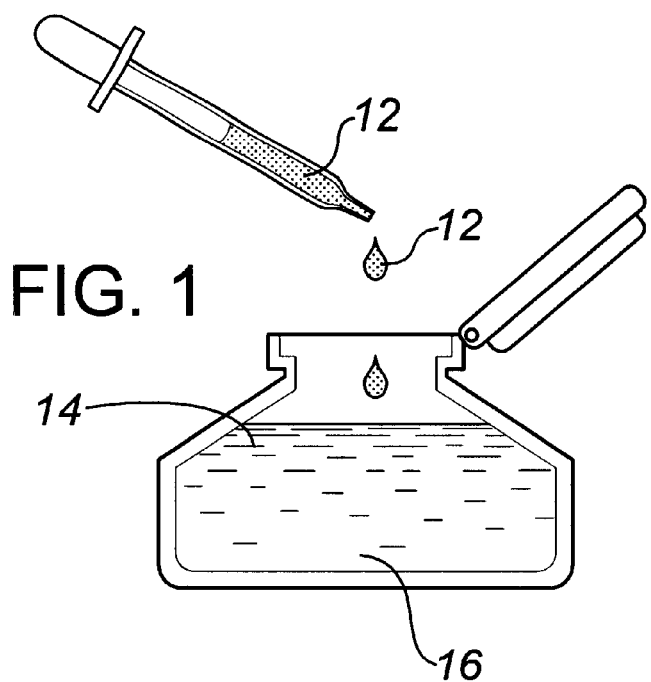
Figure 2:
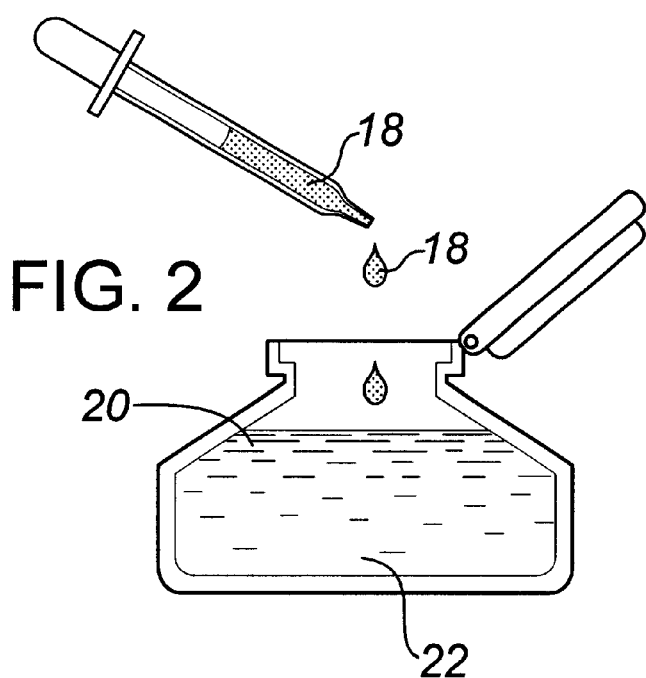
Figure 3:
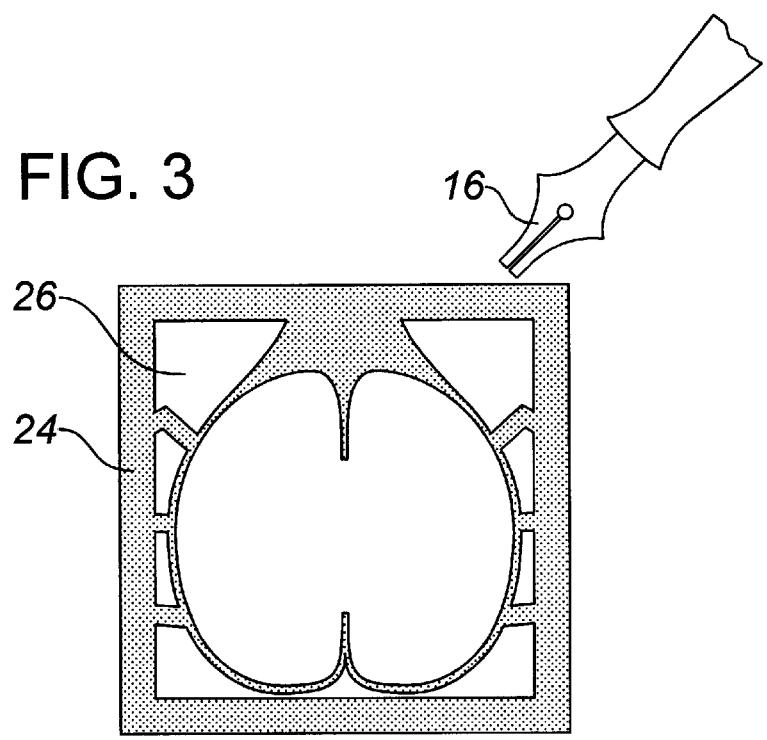
Figure 4:
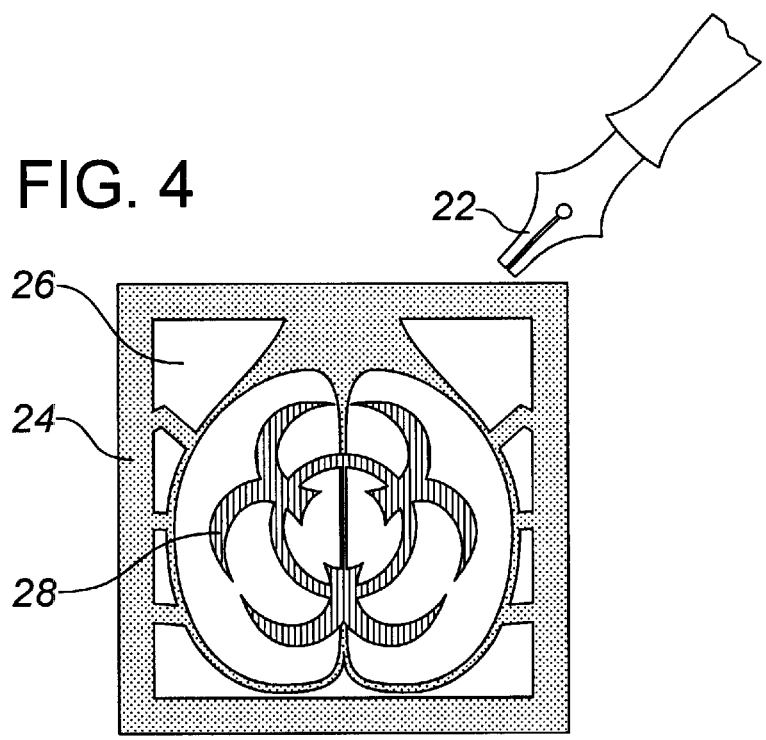

The present invention relates to a method of delivering disinfectant in an absorbent substrate.

BACKGROUND OF THE INVENTION

Canadian Patent Application 2,191,928 filed by Kenneth Reay Code on Dec. 3, 1996 discloses the use of two chemicals which when combined produce iodine disinfectant in an absorbent substrate. According to the teachings of the Code reference the two chemicals remain in a dormant state until the presence of water results in an intermixing to cause the iodine producing reaction. The Code reference was developed with respect to the transportation of vials containing diagnostic specimens of bodily fluids. Leakage of bodily fluids from the vials during transport results in an intermixing of the chemicals which releases the disinfectant.

SUMMARY OF THE INVENTION

What is required is a delivery system which will maintain the reactant chemicals in a dormant state in close proximity such that the leakage of bodily fluids will lead to the desired intermixing.

According to the present invention there is provided a method of delivering disinfectant in a absorbent substrate. A first step involves intermixing a first reactant chemical, such as anhydrous cupric sulfate, with a first ink. A second step involves intermixing a second reactant chemical, such as potassium iodine, with a second ink. A third step involves printing a first pattern on an absorbent substrate with the first ink. A fourth step involves printing a second pattern on the absorbent substrate with the second ink. The second pattern is positioned in close proximity to the first pattern, such that when the first pattern and second pattern are exposed to water an intermixing of the first reactant chemical and the second reactant chemical occurs to produce an aerosol disinfectant.

BRIEF DESCRIPTION OF THE DRAWINGS

These and other features of the invention will become more apparent from the following description in which reference is made to the appended drawings, wherein:

FIG. 1 is a side elevation view illustrating a first step of the method in accordance with the teachings of the present invention.

FIG. 2 is a side elevation view illustrating a second step of the method in accordance with the teachings of the present invention.

FIG. 3 is a top plan view illustrating a third step of the method in accordance with the teachings of the present invention.

FIG. 4 is a top plan view illustrating a fourth step of the method in accordance with the teachings of the present invention.

DETAILED DESCRIPTION OF THE PREFERRED EMBODIMENT

The preferred method of delivering disinfectant in an absorbent substrate will now be described with reference to FIGS. 1 through 4.

Referring to FIG. 1, a first step involves intermixing a first reactant chemical 12, such as anhydrous cupric sulfate, with an ink 14 to produce a first chemical doped ink 16. Referring to FIG. 2, a second step involves intermixing a second reactant chemical 18, such as potassium iodine, with an ink 20 to produce a second chemical doped ink 22. Intermixing potassium iodide with a second ink, there being two parts potassium iodide for every one part of anhydrous cupric sulfate. Referring to FIG. 3, a third step involves printing a first pattern 24 on an absorbent substrate 26 with the first chemical doped ink 16. Referring to FIG. 4, a fourth step involves printing a second pattern 28 on an absorbent substrate 26 with the second chemical doped ink 22. Second pattern 28 is positioned in close proximity to first pattern 24, such that when first pattern 24 and second pattern 28 are exposed to water an intermixing of first reactant chemical 12 and second reactant chemical 18 occurs to produce an aerosol disinfectant.

It will be apparent to one skilled in the art that there are various reactant chemicals that can be used. The reaction between anhydrous cupric sulfate and potassium iodine to produce iodine is one which is known in the art. Generally two parts potassium iodine is required for every one part of anhydrous cupric sulfate to produce the desired reaction. In order to avoid problems in implementing the invention with the chemicals described above, the following matters should be noted. When using waterbased inks, non-ferrous mixing containers and non-ferrous application instruments should be used in order to avoid galvanic depositing of copper from solution. Application on absorbent and superabsorbent substrates has been found to require an additional amount of cupric sulfate over and above that used for the reaction in the absence of the substrate. The reason for this is believed to be that the substrate has a tendency to sequester multivalent ions. Simmple titrations of the substrates with known concentrations of cupric sulfate in solution will determine the strength of cupric sulfate required to cause a drop of 0.5% potassium iodide on a previously wetted substrate to turn to dark brown. Care should be taken to consult safety data sheets relating to iodine gas before experimentation of any magnitude is conducted.

It will be apparent to one skilled in the art that modifications may be made to the illustrated embodiment without departing from the spirit and scope of the invention as hereinafter defined in the claims.

The embodiments of the invention in which an exclusive property or privilege is claimed are defined as follows:

1. A method of delivering disinfectant in an absorbent substrate, comprising the steps of:

firstly, intermixing a cupric sulfate with a first ink;

secondly, intermixing a potassium iodine with a second ink;

thirdly, printing a first pattern on an absorbent substrate with the first ink.

fourthly, printing a second pattern on the absorbent substrate with the second ink, the second pattern being in close proximity to the first pattern, such that when the first pattern and second pattern are exposed to water an intermixing of the cupric sulfate and the potassium iodine occurs to produce an aerosol disinfectant being iodine.

2. A method of delivering disinfectant in an absorbent substrate, comprising the steps of:

firstly, intermixing anhydrous cupric sulfate with a first ink;

secondly, intermixing potassium iodine with a second ink, there being two parts potassium iodine for every one part of anhydrous cupric sulfate;

thirdly, printing a first pattern on an absorbent substrate with the first ink;

fourthly, printing a second pattern on the absorbent substrate with the second ink, the second pattern being in close proximity to the first pattern, such that when the first pattern and second pattern are exposed to water an intermixing of the anhydrous cupric sulfate and the potassium iodine occurs to produce an aerosol disinfectant.

* * * * *